United States Patent [19]
Walther et al.

[11] Patent Number: 4,888,745
[45] Date of Patent: Dec. 19, 1989

[54] APPARATUS FOR MARKING INDIVIDUAL POINTS OF AN UNDERWATER CONSTRUCTION

[75] Inventors: Karl G. Walther, Schwerte; Ronald G. Walther, Aachen, both of Fed. Rep. of Germany

[73] Assignee: Magfoil & Inspektionstechniken GmbH, Lubeck, Fed. Rep. of Germany

[21] Appl. No.: 246,698

[22] Filed: Sep. 20, 1988

[30] Foreign Application Priority Data

Sep. 21, 1987 [DE] Fed. Rep. of Germany ....... 3731709

[51] Int. Cl.[4] ............................................... G01S 5/18
[52] U.S. Cl. .................................... 367/129; 324/216
[58] Field of Search ............... 367/117, 129, 130, 131; 324/215, 216; 73/588

[56] References Cited

U.S. PATENT DOCUMENTS 4,221,132 9/1980 Poole ..................................... 73/620
4,628,737 12/1986 Charles et al. ........................ 73/624
4,759,211 7/1988 Longley-Cook ..................... 324/215

FOREIGN PATENT DOCUMENTS 2372435 7/1978 France ................................ 367/117

Primary Examiner—Michael J. Tokar
Assistant Examiner—Lawrence Fess
Attorney, Agent, or Firm—Brumbaugh, Graves, Donohue & Raymond

[57] ABSTRACT

For marking and finding weld seams to be investigated under water ultrasonic transmitters 54 are provided which have luminous or light-reflecting characters 58. The diver brings an ultrasonic receiver 60 up to the ultrasonic transmitter 54. For more exact location determination along the weld seam 52 a tape is provided which is disposed along the weld seam 52 and has elements arranged in coded manner.

7 Claims, 4 Drawing Sheets

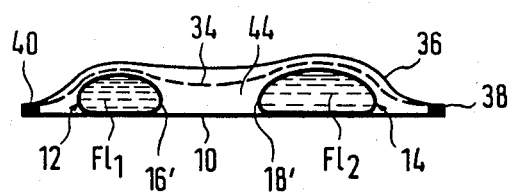
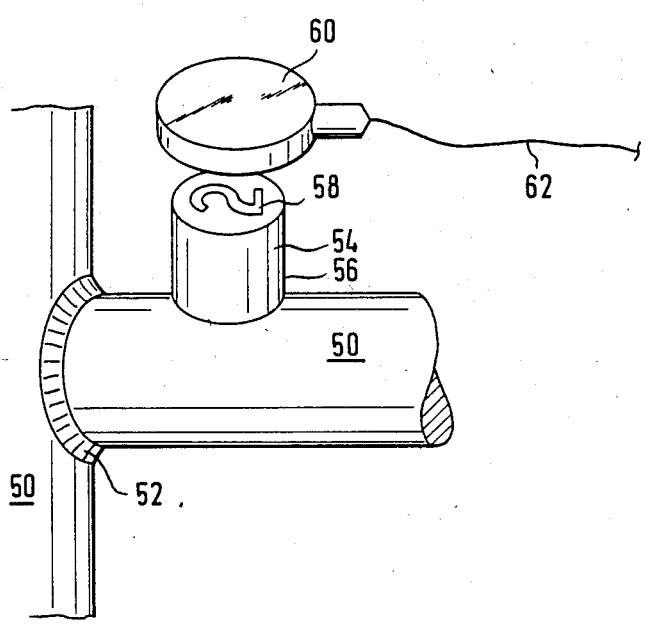

APPARATUS FOR MARKING INDIVIDUAL POINTS OF AN UNDERWATER CONSTRUCTION

The invention relates to an apparatus for marking and finding individual parts of an underwater structure or construction, such as weld seams to be investigated of an underwater pipeline or the like.

There is an increasing need to investigate the weld seams of welded underwater constructions such as pipelines or the like for cracks and other faults.

DE-PS No. 3,145,090 discloses an apparatus for investigating weld seams comprising a container having a support sheet and an inspection sheet between which particles of magnetizable material can be suspended in a liquid and in a magnetic field traversing the workpiece to be inspected and the suspension arrange themselves in characteristic manner in the presence of faults.

German patent application P No. 37 22 569.3 and P No. 37 22 596.0 propose further developments of the known apparatus.

When working under water inter alia the difficulty is encountered that the diver in the darkness at great depths has only very poor vision. Consequently, when inspecting relatively large underwater constructions confusions and mistakes may occur, for example weld seams to be inspected may be confused, incorrectly designated or not described in clearly identifiable manner.

In addition, when using the apparatuses described in DE-PS No. 3,145,090 and German patent applications P No. 37 22 569.3 and P No. 37 22 596.0 there is also the problem that when inspecting relatively long weld seams a plurality of containers must be positioned adjacent each other along the weld seam and in said containers when carrying out the investigation the magnetizable particles arrange themselves in the manner characteristic of any faults and are then fixed. The containers are then removed by the diver from the weld seam after carrying out the inspections and brought to the surface. However, to evaluate the containers and unequivocally localize the faults it is then necessary to know at which point of the weld seam the individual containers were placed when the investigation was carried out.

The invention is based on the problem of providing a reliable apparatus which is simple to handle for marking and finding individual points of an underwater structure. In addition, the invention is also based on the problem of providing an easily handled reliable apparatus with which a plurality of containers which are arranged along a weld seam and contain fixable magnetic particles can be determined and marked as regards their position with respect to a weld seam to be inspected.

The apparatus according to the invention for marking and finding individual points of an underwater construction, such as weld seams to be investigated, is characterized by a plurality of ultrasonic transmitters which are adapted to be secured to the points of the underwater construction to be marked and found and which are provided with a luminous or light-reflecting mark, and at least one ultrasonic receiver which is adapted to be positioned near one of the ultrasonic transmitters and is connected to a line via which a signal emitted by the ultrasonic transmitter can be transmitted.

Thus, according to the invention initially in a first working step all the points of an underwater construction to be investigated can each be provided with an ultrasonic transmitter which is adapted to be secured directly to the underwater construction. Subsequently a diver can easily find his bearings by these ultrasonic transmitters because they are provided with luminous or light-reflecting markings such as numbers or letters. It is possible at the same time to report the point at which the diver happens to be working to the persons on deck of the assisting ship by the diver positioning an ultrasonic receiver directly on the ultrasonic transmitter secured to the underwater construction so that the receiver conducts signals received from the ultrasonic transmitter via a line to the ship's deck. For unique allocation and marking of the individual points of the underwater construction the ultrasonic transmitters can each either transmit different frequencies or the signal emitted by them can be coded in a characteristic manner in each case.

The ultrasonic transmitter is preferably so designed that it comprises a permanent magnet so that it can readily be magnetically secured to a ferromagnetic material.

If a weld seam has been marked in the manner described above by means of an ultrasonic transmitter then in a following working step a diver can easily find and identify this weld seam. If this weld seam is now to be investigated for cracks or other faults by means of a plurality of containers of the type mentioned at the beginning then the location of the individual containers over the weld seam is determined in accordance with a further development of the invention in that an elongated tape is secured along the weld seam, for example starting from the ultrasonic transmitter disposed at the uppermost point of the weld seam. The tape or ribbon is provided in the direction of its longitudinal extent with elements arranged in coded manner and comprising a material of high magnetic permeability. The elements are coded with respect to their location, i.e. they are configured or arranged in a manner characteristic of the particular location along the tape, there obviously being a great number of possibilities for doing this.

If now the known containers with the magnetic particles are placed on the weld seam and the known inspection made then not only do the faults in the weld seam effect a characteristic alignment of the magnetic particles in the containers but in addition the elements arranged in coded manner and comprising highly permeable material with minimum remanence generate an alignment of the magnetizable particles characteristic of the location of the container with respect to the tape and thus with respect to the weld seam and this characteristic alignment is also thereafter fixed in a manner known per se. The containers subsequently removed from the weld seam and brought on deck thus exhibit not only a characteristic alignment of the magnetic particles corresponding to the faults of the weld seam but in addition also a structure of the magnetic particles characteristic of their location with respect to the weld seam.

In a preferred further development of such an apparatus the band or tape is provided with luminous or light-reflecting markings so that the diver, after the tape has been secured parallel to the weld seam, can easily find his bearings with the aid of the luminous or light-reflecting markings. If in accordance with a preferred further development of the invention the markings are spaced from each other a distance corresponding to the length of a container then in simple manner the diver can position a container adjacent each marking; for example, he brings the centre line (or another marking) of the container directly to bear on the luminous or light-reflecting marking of the tape.

The elements of the tape arranged in coded manner are preferably formed by short wire pieces of highly permeable material of low remanence. The wire pieces may be fused into the tape at regular intervals. It is obvious that the tape itself consists of a material which is magnetically inactive, for example plastic.

In a preferred further development of the invention the tape is secured along the weld seam in that in the tape a plurality of pockets is provided into which permanent magnets may be inserted which hold the tape on the weld seam to be investigated.

Hereinafter an example of embodiment of the invention will be explained in detail with the aid of the drawings, wherein:

FIG. 2 is a section along the line I-II of FIG. 1;

FIG. 3 is an apparatus for marking and finding individual points of an underwater construction;

Figure 1:
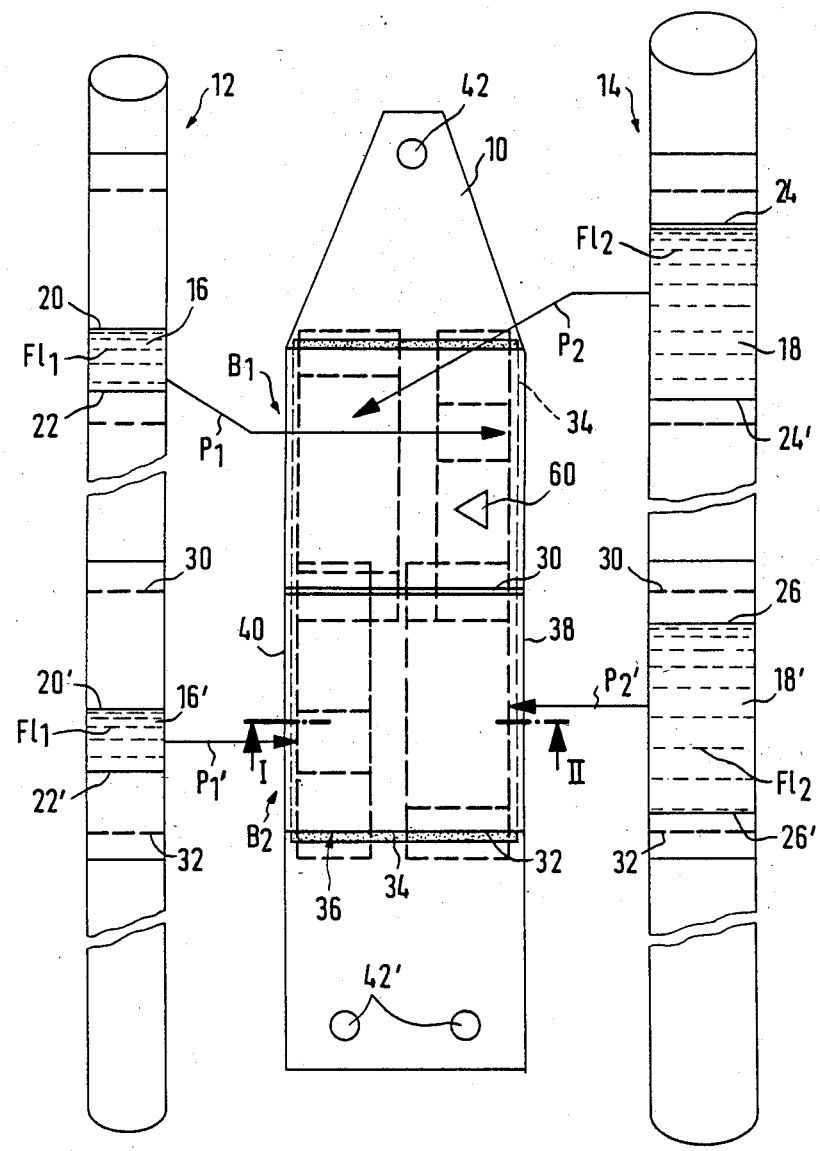
FIG. 1 is a schematic illustration of an apparatus for inspecting metal workpieces.

FIGS. 1 and 2 show a means for inspecting workpieces, in particular weld seams, for cracks and the like which is used in the apparatus according to the invention for marking and finding individual points of an underwater construction and is defined and marked according to the invention with regard to its position with respect for example to a weld seam. These Figures correspond to German patent application P No. 37 22 596.0.

FIG. 1 shows a support sheet 10 of plastic and two hoses 12 and 14, also of plastic. In the hoses 12 and 14 shown in FIG. 1 on the left and right of the support sheet 10 liquid chambers 16, 16', 18, 18'0 are formed. By welded or adhered seams 20, 20', 22, 22', 24, 24', 26 and 26' the individual chambers are defined in the two hoses 12 and 14.

A liquid $FL_1$ is contained in each of the chambers 16, 16'. In the example of embodiment illustrated the liquid $FL_1$ is deionised water. In the chambers 18, 18' an alkaline solution $Fl_2$ of nesosilicates is contained.

In the production of the ready-to-use apparatus for inspecting metal workpieces the chambers 16, 16', 18, 18' formed in the hoses 12 and 14 respectively are positioned on the support sheet 10 in accordance with the arrows $P_1$, $P_{1'}$, $P_2$ and $P_{2'}$.

In accordance with FIGS. 1 and 2 over the chambers 16, 16', 18, 18' arranged on the support sheet 10 a continuous net of plastic is placed and over the net a transparent inspection foil 36, likewise of plastic. In accordance with FIGS. 1 and 2 the support sheet 10, the net or meshing 34 and the inspection sheet 36 are then joined together along the weld seams 38 and 40. The chambers 16, 16', 18, 18' are likewise joined to the support sheet 10 by welding or adhering to projecting hose portions. Reference numerals 42, 42' designate holes.

Furthermore, between the inspection sheet 36 and the net 34 adjacent the chambers 16, 16' containing the deionised water in each case compacted and evacuated pellets of a powder containing carbonyl iron, zinc oxide and white cement are arranged (not shown).

In accordance with FIG. 1 on the support sheet 10 two containers $B_1$, $B_2$ are formed which are separated by the weld seam 30 and which each contain a chamber with the liquid $FL_1$, a chamber with the liquid $FL_2$ and the pellet.

As apparent from FIG. 1 in the two adjacent containers $B_1$, $B_2$ separated by the weld seam 30 the chambers with the different liquids $Fl_1$ and $Fl_2$ are arranged "crosswise", i.e. in the upper container $B_1$ the chamber 18 is arranged on the left in accordance with the arrow $P_2$ and the chamber 16 on the right in accordance with the arrow $P_1$ whilst in the container $B_2$ beneath the weld seam 30 the chambers 16' and 18' are arranged to the left and right respectively in accordance with the arrows $P_1$ and $P_2$. Reference numeral 32 designates another weld seam.

To perform an inspection of the weld seam for cracks or other faults the support sheet is placed by the diver under water onto the weld seam to be investigated in such a manner that the inspection sheet 36 lies directly on the weld seam, i.e. the support sheet 10 is remote from the weld seam. Beforehand, the diver has caused to burst mechanically by pressure the chamber 16, 16' containing the deionised water $Fl_1$ so that in the main chamber 44 (FIG. 2) formed between the support sheet 10 and the inspection sheet 36 the powder pellet is dissolved in the dionised water.

In a manner known per se the diver then places a magnetizing means onto the workpiece to be investigated in such a manner that a magnetic field passes both through the weld seam to be investigated and through the suspension of the particles of magnetizable material (in this case carbonyl iron). The particles arrange themselves in the magnetic field and in the presence of faults form characteristic structures, such as grooves, agglomerations, etc., which can later be analyzed by the expert.

Since in the suspension of dionised water and the powder mixture containing zinc oxide, white cement and carbonyl iron no viscosity change has yet occurred, the powder particles are freely movable and can align themselves in the magnetic field very rapidly, for example within one second. When placing the support sheet over the weld seam and positioning the magnetizing device the diver is not subjected to any time restrictions whatever. Only when these operations have been concluded does the diver open the chambers 18, 18' by pressure so that the liquid $Fl_1$, i.e. the alkaline solution of nesosilicates, penetrates into the suspension and there causes a change of state on the basis of which the aligned particles of magnetizable material are fixed in their position characteristic of any faults present. The plastic mesh 34 promotes the fixing of the particles so that after the change of state in the suspension (in this case a silicification) the support sheet 10 can be removed from the weld seam investigated and brought on deck without the characteristic arrangement of the particles being disturbed.

FIG. 3 shows an underwater construction 50 having two parts connected by a weld seam 52.

For marking, finding again and identifying the weld seam 52 an ultrasonic transmitter 54 is secured to the underwater construction 50. For the securing a permanent magnet is provided which is arranged at 56 in the ultrasonic transmitter 54 and clings to the underwater construction 50.

At its upper side the ultrasonic transmitter 54 comprises a marking in the form of a digit 58. The digit 58 consists of fluorescent material. On its upper side beneath the digit 58 the ultrasonic transmitter 54 is provided with a piezocrystal for generating ultrasonic waves. Furthermore, the ultrasonic transmitter 54 includes a control circuit known per se for generating ultrasonic waves.

To find and identify the weld seam 52 in the course of a subsequent working operation the diver goes by the digit 58 of the ultrasonic transmitter 54. In addition the diver carries with him an ultrasonic receiver 60 and places this directly above the digit 58, i.e. in the vicinity of the piezocrystal disposed there and generating the ultrasonic waves. The ultrasonic waves emitted by the ultrasonic transmitter 54 are coded either by means of their frequency or the signal sequence and are received by the ultrasonic receiver 60 and transmitted via a line 62 to the deck of the ship attending the diver.

Figure 4:
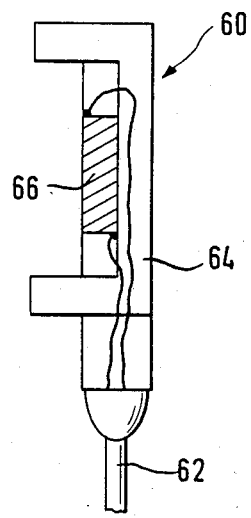
FIG. 4 is a section through an ultrasonic receiver.

FIG. 4 shows the ultrasonic receiver in section. In a housing 64 an ultrasonic microphone 66 known per se is disposed and disconnected to the ultrasonic line 62.

Once the diver has recognized the weld seam 52 by means of the ultrasonic transmitter 54 and the digit 58 he can start checking the weld seam 52 for faults.

Figure 5:
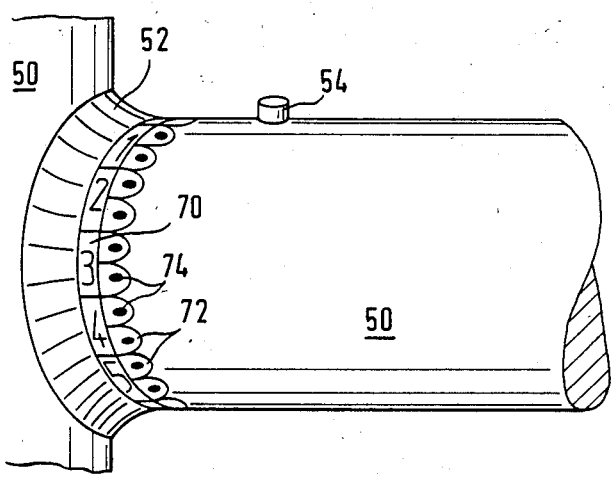
FIG. 5 is an underwater construction having a tape applied along a weld seam.

For this purpose in accordance with FIG. 5 a tape 70 is placed adjacent the weld seam 52 on the underwater construction 50 and secured there. For the securing permanent magnets 74 are provided which are arranged in pockets 72 of the tape or ribbon, see also FIG. 6.

The weld seam 52 is now investigated for faults employing means as known from cited DE-PS No. 3,145,090 and the German patent applications P No. 37 22 569 and P No. 37 22 596 and described above with the aid of FIGS. 1 and 2.

Figure 6:
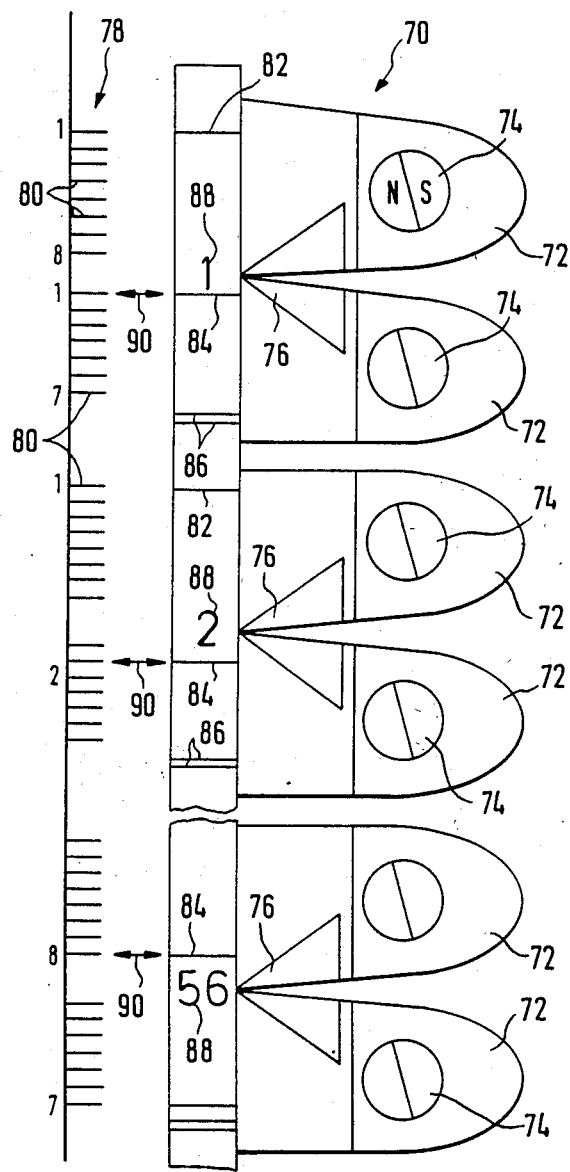
FIG. 6 shows the tape of FIG. 5 in detail.

In accordance with FIG. 6 the tape 70 is provided with luminous or reflecting arrows 76. The tape 70 comprises individual segments each corresponding to a container $B_1$ and $B_2$.

On the side of the tape 70 opposite the pockets 72 a coding 78 is provided in the form of individual elements 80. The elements 80 consist of short wire pieces of highly permeable material which has a very low magnetic remanence. On magnetization (as described above with reference to FIGS. 1 and 2) magnetic poles therefore form at the ends of the elements 80 and the particles of magnetizable material are attracted by said poles. As a result at the ends of the elements 80 in the containers clearly apparent structures appear which when the measurement has been carried out like the particle structures characteristic of any faults are fixed on hardening and can subsequently be interpreted.

The tape 70 is divided so that the individual containers with the magnetizable particles cover the weld seam 52 without any gaps. A slight overlapping of the individual containers may also be provided.

Each container is placed with a centre seam (e.g. the weld seam 30 according to FIG. 1) on the weld seam 52 in such a manner that the centre seam comes to lie exactly on the tip of one of the arrows 76. According to FIG. 6 individual wire pieces 82 and 84 are arranged in the tape 70 in such a manner that for each container a first wire piece 82 lies at the beginning (seen from above) and coincides with the "1" of the coding 78. The respective lower wire piece 84 is offset with respect to the upper wire piece 82 in such a manner that in the first container the lower wire piece 84 coincides with the "1" of the coding whilst in the following container "2" (see the marking 88) the lower wire rod 84 coincides with the "2" of the coding 78. The assignment between the wire rods 84 and the coding 78 is indicated by arrows 90 in FIG. 6. The end of a container is marked by double wire pieces 86 in each case. Since the coding 78 and the wire rods 82, 84 and 86 generate in the containers a distinct structure change it is possible with them to obtain a complete location determination of the individual containers with respect to their order and the weld seam 52.

We claim:

1. An apparatus for marking and finding individual points of an underwater construction, such as weld seams to be investigated of an underwater pipeline or the like, characterized by a plurality of ultrasonic transmitters which are adapted to be secured to the points of the underwater construction to be marked and found and which are provided with a luminous mark, and at least one ultrasonic receiver which is adapted to be positioned near one of the ultrasonic transmitters and is connected to a line via which a signal emitted by the ultrasonic transmitter can be transmitted.

2. The apparatus according to claim 1, characterized in that the ultrasonic transmitters each comprise a permanent magnet.

3. The apparatus according to claims 1 or 2, characterized in that the ultrasonic transmitters each transmit at a different frequency and the signal emitted by them is differently coded in each case.

4. An apparatus for determining and marking the position of a plurality of containers with respect to a weld seam under water, said containers holding a suspension of particles of magnetizable material in a liquid, wherein in a magnetic field traversing the weld seam the suspension arranges in characteristic manner in the presence of faults, characterized by a tape adapted to be secured along the weld seam which comprises a series of elements arranged longitudinally along the tape in coded manner, said elements comprising a material with magnetic permeability.

5. The apparatus according to claim 4, characterized in that the tape comprises luminous markings with respect to which said containers can be positioned.

6. The apparatus according to claims 4 or 5, characterized in that the elements arranged in coded manner consist of pieces of wire.

7. The apparatus according to claim 4, characterized in that the tape further comprises a plurality of permanent magnets with which it can be secured along the weld seam.

* * * * *